United States Patent
Hiltner et al.

(10) Patent No.: US 9,549,679 B2
(45) Date of Patent: Jan. 24, 2017

(54) MULTIPLE TRANSDUCER DELIVERY DEVICE AND METHOD

(71) Applicant: ACIST MEDICAL SYSTEMS, INC., Eden Prairie, MN (US)

(72) Inventors: Jason F Hiltner, Minnetonka, MN (US); Kendall R. Waters, Livermore, CA (US); Thomas C. Moore, Livermore, CA (US); Robert Zelenka, Milpitas, CA (US)

(73) Assignee: ACIST Medical Systems, Inc., Eden Prairie, MN (US)

( * ) Notice: Subject to any disclaimer, the term of this patent is extended or adjusted under 35 U.S.C. 154(b) by 330 days.

(21) Appl. No.: 13/834,031

(22) Filed: Mar. 15, 2013

(65) Prior Publication Data
US 2013/0303914 A1    Nov. 14, 2013

Related U.S. Application Data

(60) Provisional application No. 61/646,561, filed on May 14, 2012.

(51) Int. Cl.
*A61B 5/0215* (2006.01)
*A61B 8/12* (2006.01)
(Continued)

(52) U.S. Cl.
CPC ......... *A61B 5/0215* (2013.01); *A61B 5/02158* (2013.01); *A61B 5/1076* (2013.01);
(Continued)

(58) Field of Classification Search
None
See application file for complete search history.

(56) References Cited

U.S. PATENT DOCUMENTS 4,523,471 A * 6/1985 Lee ............... G01N 29/24
                                            310/334
4,587,975 A    5/1986 Salo et al.
(Continued)

FOREIGN PATENT DOCUMENTS

CN      101854853 A    10/2010
EP       1025805 A1     8/2000
(Continued)

OTHER PUBLICATIONS

International Searching Authority, Notification of Transmittal of the International Searh Report and the Written Opinion of the International Searching Authority, or the Declaration, (co-pending) International Application No. PCT/US2013/040765; Jul. 22, 2013. 13 pages, European Patent Office, Rijswijk, The Netherlands.
(Continued)

*Primary Examiner* — Long V Le
*Assistant Examiner* — Kevin Pontius
(74) *Attorney, Agent, or Firm* — Fredrikson & Byron, P.A.

(57) ABSTRACT

A stenotic lesion can be characterized by measuring both pressure drop across the stenotic lesion and the size of the vessel lumen adjacent the stenotic lesion, both with sensors delivered intravascularly to the stenotic lesion site. The size (e.g., inner diameter, cross-sectional profile) of the vessel lumen adjacent the stenotic lesion can be measured via one or more intravascular ultrasound transducers. Such one or more intravascular ultrasound transducer(s) can be delivered to the site of the stenotic lesion with the same delivery device that carries a pressure transducer.

11 Claims, 14 Drawing Sheets

(51) Int. Cl.
*A61B 5/107* (2006.01)
*A61B 8/00* (2006.01)
(52) U.S. Cl.
CPC ............... *A61B 8/12* (2013.01); *A61B 8/445* (2013.01); *A61B 8/4483* (2013.01); *A61B 5/02154* (2013.01)

(56) References Cited

U.S. PATENT DOCUMENTS

| | | | |
|---|---|---|---|
| 4,928,693 | A | 5/1990 | Goodin et al. |
| 5,829,439 | A * | 11/1998 | Yokosawa ............ A61B 5/6848 |
| | | | 600/461 |
| 6,010,511 | A | 1/2000 | Murphy |
| 6,083,170 | A * | 7/2000 | Ben-Haim ................. 600/463 |
| 6,372,498 | B2 * | 4/2002 | Newman et al. ............ 435/455 |
| 7,454,244 | B2 | 11/2008 | Kassab et al. |
| 7,818,053 | B2 | 10/2010 | Kassab |
| 7,963,929 | B2 | 6/2011 | Kassab |
| 8,078,274 | B2 | 12/2011 | Kassab |
| 8,082,032 | B2 | 12/2011 | Kassab et al. |
| 8,099,161 | B2 | 1/2012 | Kassab |
| 8,114,143 | B2 | 2/2012 | Kassab et al. |
| 9,259,161 | B2 | 2/2016 | Suchecki et al. |
| 2004/0097806 | A1 | 5/2004 | Hunter et al. |
| 2004/0230131 | A1 | 11/2004 | Kassab et al. |
| 2005/0203434 | A1 | 9/2005 | Kassab |
| 2006/0074318 | A1 * | 4/2006 | Ahmed et al. ................ 600/465 |
| 2006/0241482 | A1 * | 10/2006 | Karasawa ................ A61B 8/12 |
| | | | 600/466 |
| 2007/0129717 | A1 | 6/2007 | Brown et al. |
| 2007/0264732 | A1 * | 11/2007 | Chen ...................... A61B 1/041 |
| | | | 600/459 |
| 2008/0033316 | A1 | 2/2008 | Kassab et al. |
| 2008/0161696 | A1 * | 7/2008 | Schmitt ............... A61B 5/0066 |
| | | | 600/467 |
| 2008/0194996 | A1 | 8/2008 | Kassab |
| 2008/0234658 | A1 | 9/2008 | Kassab et al. |
| 2008/0294041 | A1 | 11/2008 | Kassab |
| 2009/0082698 | A1 | 3/2009 | Kassab |
| 2009/0118637 | A1 | 5/2009 | Kassab et al. |
| 2009/0171201 | A1 | 7/2009 | Olson |
| 2009/0182287 | A1 | 7/2009 | Kassab |
| 2009/0204029 | A1 | 8/2009 | Kassab |
| 2009/0204134 | A1 | 8/2009 | Kassab |
| 2009/0216133 | A1 | 8/2009 | Kassab |
| 2009/0299360 | A1 * | 12/2009 | Ormsby .......................... 606/33 |
| 2009/0319020 | A1 | 12/2009 | Kassab |
| 2010/0010355 | A1 | 1/2010 | Kassab |
| 2010/0010368 | A1 | 1/2010 | Kassab |
| 2010/0010488 | A1 | 1/2010 | Kassab et al. |
| 2010/0010503 | A1 | 1/2010 | Kassab |
| 2010/0030055 | A1 | 2/2010 | Kassab |
| 2010/0152607 | A1 | 6/2010 | Kassab |
| 2010/0168836 | A1 | 7/2010 | Kassab |
| 2010/0174271 | A1 | 7/2010 | Kassab |
| 2010/0222786 | A1 | 9/2010 | Kassab |
| 2010/0234698 | A1 | 9/2010 | Manstrom et al. |
| 2010/0249588 | A1 | 9/2010 | Knight |
| 2011/0034824 | A1 | 2/2011 | Kassab |
| 2011/0178383 | A1 | 7/2011 | Kassab |
| 2011/0178417 | A1 | 7/2011 | Kassab |
| 2011/0196255 | A1 | 8/2011 | Kassab |
| 2011/0196282 | A1 | 8/2011 | Kassab |
| 2011/0208109 | A1 | 8/2011 | Kassab |
| 2011/0245860 | A1 | 10/2011 | Kassab |
| 2011/0313341 | A1 | 12/2011 | Kassab |
| 2012/0053441 | A1 | 3/2012 | Kassab |
| 2012/0191181 | A1 | 7/2012 | Kassab et al. |
| 2012/0197113 | A1 * | 8/2012 | Courtney ................. A61B 8/12 |
| | | | 600/427 |
| 2012/0277725 | A1 | 11/2012 | Kassab et al. |
| 2012/0287750 | A1 * | 11/2012 | Deladi ................ A61B 5/0084 |
| | | | 367/7 |
| 2012/0289951 | A1 | 11/2012 | Kassab et al. |
| 2012/0296368 | A1 | 11/2012 | Kassab et al. |
| 2013/0216114 | A1 | 8/2013 | Courtney et al. |
| 2014/0180083 | A1 | 6/2014 | Hoseit |

FOREIGN PATENT DOCUMENTS

| | | | |
|---|---|---|---|
| WO | 9744089 A1 | 11/1997 | |
| WO | 9835611 A1 | 8/1998 | |
| WO | WO 9934724 A2 * | 7/1999 | ........... A61B 5/0285 |
| WO | 2006037082 A2 | 4/2006 | |
| WO | 2008005388 A2 | 1/2008 | |

OTHER PUBLICATIONS

Notification of Transmittal of the International Search Report and the Written Opinion of the International Searching Authority, or the Declaration for PCT/US2014/046374, Mar. 27, 2015, 13 pages, International Searching Authority, European Patent Office Rijswijk, The Netherlands.

* cited by examiner

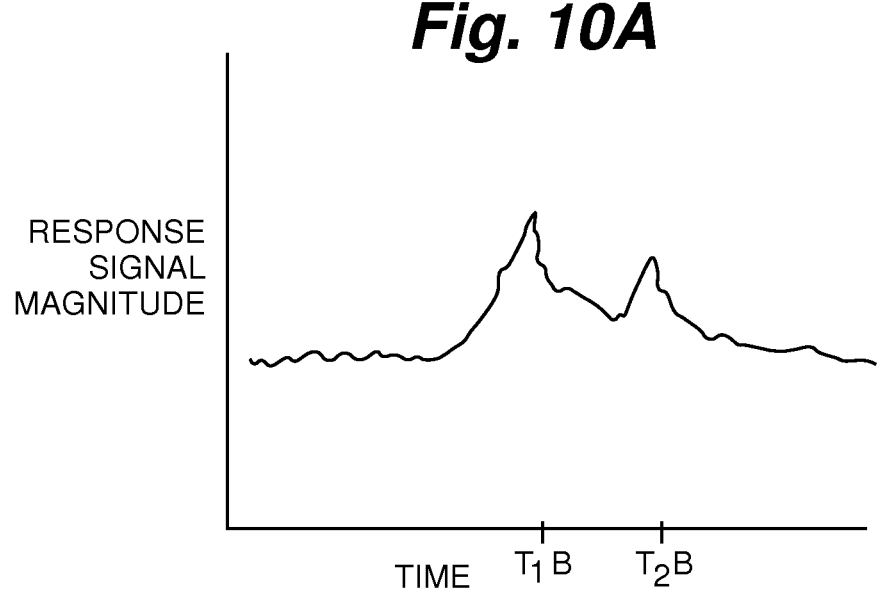
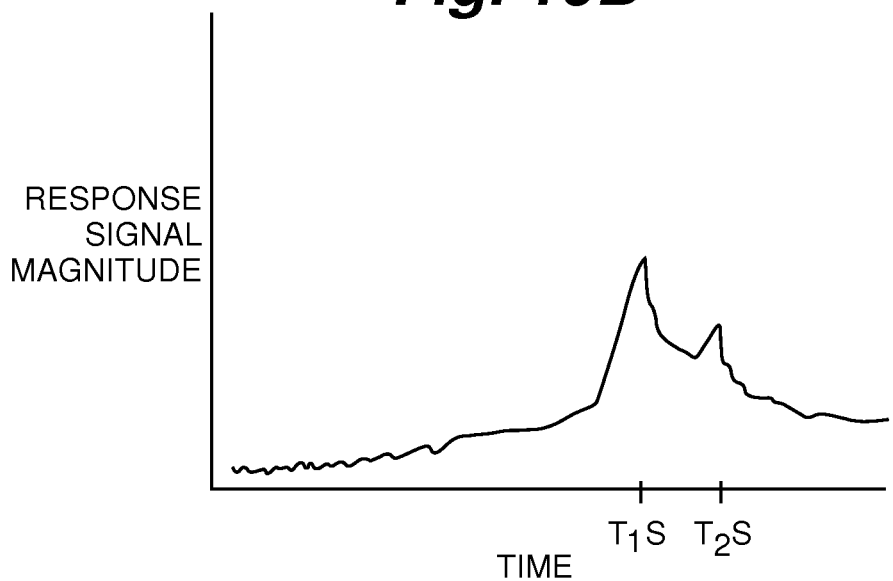

MULTIPLE TRANSDUCER DELIVERY DEVICE AND METHOD

TECHNICAL FIELD

This disclosure relates to methods and devices for assessing the severity of a stenotic lesion in a patient's vasculature.

BACKGROUND

Assessing the severity of a stenotic lesion is an important part of recommending a treatment option. In some instances, if the stenotic lesion is permitted to grow unchecked, it can lead to a blockage of blood flow which can cause a variety of very significant problems. Common treatment options, such as a stent, angioplasty, etc. are often recommended to inhibit or roll back growth of a stenotic lesion. That said, treatment options can result in their own negative consequences. Thus, if the characteristics of the stenotic lesion are such that they have a minimal impact on the flow of blood through the vessel, it may be recommended to monitor the stenotic lesion over time but take no intervening action other than to administer drug therapy. Angiograms are common methods of assessing the severity of a stenotic lesion, but, in many cases, there is a desire for additional means of gathering information to more fully characterize the stenotic lesion.

SUMMARY

Embodiments of the present invention allow more full characterization of a stenotic lesion by measuring both pressure drop across the stenotic lesion and the size of the vessel lumen adjacent the stenotic lesion, both with sensors delivered intravascularly to the stenotic lesion site. In preferred embodiments, the size (e.g., inner diameter, cross-sectional profile) of the vessel lumen adjacent the stenotic lesion can be measured via one or more intravascular ultrasound transducers. In preferred embodiments, the intravascular ultrasound transducer(s) can be delivered to the site of the stenotic lesion with the same delivery device that carries the pressure transducer(s).

In some embodiments, an intravascular transducer delivery device for use with a patient is provided. The intravascular transducer delivery device can include a distal sleeve, which can have a guidewire lumen for slidably receiving a medical guidewire. The intravascular transducer delivery device can include a proximal portion that may be coupled to the distal sleeve. The intravascular transducer delivery device can include a first pressure transducer, which can be coupled to the distal sleeve and/or the proximal portion. The first pressure transducer may be adapted to take a first intravascular fluid pressure measurement and generate a first pressure signal representative of the first intravascular fluid pressure measurement. The intravascular transducer delivery device may include a first pressure transducer conductor in communication with the first pressure transducer. The first pressure transducer conductor may be adapted to communicate the first pressure signal outside of the patient through the proximal portion. The intravascular transducer delivery device may include a first ultrasound transducer, which can be coupled to the distal sleeve and/or the proximal portion. The first ultrasound transducer may be adapted to take a first intravascular physical dimension measurement and generate a first ultrasound signal representative of the first intravascular physical dimension measurement. The intravascular transducer delivery device may include a first ultrasound transducer conductor in communication with the first ultrasound transducer. The first ultrasound transducer conductor can be adapted to communicate the first ultrasound signal outside of the patient through the proximal portion.

Some embodiments of the intravascular transducer delivery device may have one or more of the following features. In some embodiments, the first pressure transducer may be a fiber optic pressure transducer. Some embodiments may include a second pressure transducer coupled to the distal sleeve and/or the proximal portion. In some such embodiments, the second pressure transducer can be adapted to take a second intravascular fluid pressure measurement and generate a second pressure signal representative of the second intravascular fluid pressure measurement. In some such embodiments, the second pressure transducer may be spaced axially in the vessel lumen from the first pressure transducer by a distance that corresponds to a stenotic lesion. In some embodiments, the first pressure transducer can be coupled to the distal sleeve. In some embodiments, the first ultrasound transducer may include an ultrasound transducer ring. In some embodiments, the first ultrasound transducer can be coupled to the distal sleeve. In some embodiments, the first ultrasound transducer may be positioned distal to the first pressure transducer. In some embodiments, the first intravascular physical dimension measurement can include a radial distance from the first ultrasound transducer to a vessel wall.

Some embodiments of the intravascular transducer delivery device may include a second ultrasound transducer and/or a third ultrasound transducer, both coupled to the distal sleeve and/or the proximal portion. In such embodiments, the second ultrasound transducer can be adapted to take a second intravascular physical dimension measurement and generate a second ultrasound signal representative of the second intravascular physical dimension measurement. In such embodiments, the third ultrasound transducer can be adapted to take a third intravascular physical dimension measurement and generate a third ultrasound signal representative of the third intravascular physical dimension measurement. In such embodiments, the first ultrasound transducer, the second ultrasound transducer, and the third ultrasound transducer may be spaced about a circumference of the distal sleeve and/or the proximal portion approximately 120° from one another. In some such embodiments, the first ultrasound transducer conductor may in communication with the second ultrasound transducer and the third ultrasound transducer. In some such embodiments, the first ultrasound transducer conductor may be adapted to communicate the second ultrasound signal and the third ultrasound signal outside of the patient through the proximal portion. In some embodiments, the intravascular transducer delivery device may include a second ultrasound transducer conductor in communication with the second ultrasound transducer. In some such embodiments, the second ultrasound transducer conductor may be adapted to communicate the second ultrasound signal outside of the patient through the proximal portion. In some embodiments, the intravascular transducer delivery device may include a third ultrasound transducer conductor in communication with the third ultrasound transducer. In some such embodiments, the third ultrasound transducer conductor may be adapted to communicate the third ultrasound signal outside of the patient through the proximal portion.

In some embodiments, a method of gathering information about a stenotic lesion is provided. Some embodiments involve sliding an intravascular transducer delivery device over a medical guidewire to position a first pressure transducer and a first ultrasound transducer near the stenotic lesion. Some embodiments involve taking a first intravascular fluid pressure measurement near the stenotic lesion with the first pressure transducer. Some embodiments involve taking a first intravascular physical dimension measurement near the stenotic lesion with the first ultrasound transducer. Some preferred embodiments involve taking the first intravascular fluid pressure measurement and the first intravascular physical dimension measurement contemporaneously (e.g., close enough together in time to preclude (a) positioning a pressure transducer near the stenotic lesion, (b) taking the intravascular fluid pressure measurement (commonly under hyperemic conditions), (c) withdrawing the pressure transducer from the patient's body, (d) inserting an ultrasound transducer into the patient's body, (e) positioning the ultrasound transducer near the stenotic lesion, and (f) taking the intravascular physical dimension measurement). In some embodiments, the first intravascular fluid pressure measurement and the first intravascular physical dimension measurement may be taken, e.g., within two minutes, one and a half minutes, one minute, 50 seconds, 40 seconds, 30 seconds, 20 seconds, or 10 seconds of one another.

Some embodiments of the method of gathering information about a stenotic lesion may have one or more of the following features. In some embodiments, the first intravascular fluid pressure measurement may be taken from a location distal to the stenotic lesion. In some embodiments, the method can further include using the first intravascular fluid pressure measurement to assess pressure drop across the stenotic lesion. In some such embodiments, assessing pressure drop across the stenotic lesion may include calculating FFR or iFR. In some embodiments, the method may further include using the first intravascular physical dimension measurement to calculate a diameter or cross-sectional profile of the vessel lumen adjacent the stenotic lesion and/or using the first intravascular fluid pressure measurement to assess pressure drop across the stenotic lesion. In some embodiments, the method may further include taking (e.g., contemporaneously) a second intravascular physical dimension measurement near the stenotic lesion with the first ultrasound transducer. In some such embodiments, the second intravascular physical dimension measurement may be taken from a second location that is axially spaced in the vessel lumen from a first location at which the first intravascular physical dimension measurement is taken. In some embodiments, the method may further include using the first intravascular physical dimension measurement to calculate a first diameter or a first cross-sectional profile of the vessel lumen at the first location. In some embodiments, the method may further include using the second intravascular physical dimension measurement to calculate a second diameter or a second cross-sectional profile of the vessel lumen at the second location. In some such embodiments, an axial profile of the vessel lumen's diameter and/or cross-sectional area adjacent the stenotic lesion may be taken. In some embodiments, the method may further include displaying information regarding pressure drop across the stenotic lesion based on the first intravascular fluid pressure measurement. In some embodiments, the method may further include displaying information regarding a diameter or cross-sectional profile of the vessel lumen adjacent the stenotic lesion based on the first intravascular physical dimension measurement. In some preferred embodiments, the displaying may be on an injection system control panel. In some embodiments, the method may further include withdrawing the intravascular transducer delivery device over the medical guidewire without withdrawing the medical guidewire. In some embodiments, the method may further include deploying an interventional therapy device to the stenotic lesion using the same medical guidewire.

In some embodiments, one or more additional transducers may be positioned near the stenotic lesion. In some embodiments, sliding the intravascular transducer delivery device over the medical guidewire may further position a second pressure transducer near the stenotic lesion. In some such embodiments, the method may further include taking a second intravascular fluid pressure measurement near the stenotic lesion with the second pressure transducer. In some preferred embodiments, the second intravascular fluid pressure measurement may be contemporaneous with the first intravascular fluid pressure measurement and the first intravascular physical dimension measurement. In some embodiments, the first intravascular fluid pressure measurement may be taken from a first location that is distal to the stenotic lesion. In some embodiments, the second intravascular fluid pressure measurement may be taken from a second location that is proximal to the stenotic lesion. In some embodiments, the method may further include using the first intravascular fluid pressure measurement and the second intravascular fluid pressure measurement to assess pressure drop across the stenotic lesion. In some embodiments, sliding the intravascular transducer delivery device over the medical guidewire may further position a second ultrasound transducer and a third ultrasound transducer near the stenotic lesion. In some embodiments, the method may further include taking a second intravascular physical dimension measurement near the stenotic lesion with the second ultrasound transducer and a third intravascular physical dimension measurement near the stenotic lesion with the third ultrasound transducer. In some preferred embodiments, the second intravascular physical dimension measurement and the third intravascular physical dimension measurement are taken contemporaneously with each other and with the first intravascular fluid pressure measurement and the first intravascular physical dimension measurement. In some embodiments, the method may further include using the first intravascular physical dimension measurement, the second intravascular physical dimension measurement, and the third intravascular physical dimension measurement to calculate a diameter or cross-sectional profile of the vessel lumen adjacent the stenotic lesion.

In some embodiments, a fluid injection system is provided. The fluid injection system can include fluid tubing adapted to provide fluid communication between the fluid injection system and a patient. The fluid injection system can include a processor adapted to receive a first pressure signal representative of a first intravascular fluid pressure measurement taken near a stenotic lesion of the patient. In some embodiments, the processor can be adapted to receive a first ultrasound signal representative of a first intravascular physical dimension measurement taken near the stenotic lesion. In some embodiments, the processor may be adapted to receive the first pressure signal and the first ultrasound signal contemporaneously (e.g., within two minutes, one and a half minutes, one minute, 50 seconds, 40 seconds, 30 seconds, 20 seconds, or 10 seconds of one another). Some fluid injection systems may include a control panel. The control panel may be adapted to receive from the processor a first set of pressure information based on the first intravascular fluid pressure measurement and/or a first set of ultrasound information based the first intravascular physical dimension measurement. The control panel may be adapted to display the first set of pressure information and the first set of ultrasound information.

Some embodiments of the fluid injection system may have one or more of the following features. In some embodiments, the first intravascular fluid pressure measurement may be taken from a location distal to the stenotic lesion. In some embodiments, the first set of pressure information may include information regarding pressure drop across the stenotic lesion. In some instances, the first set of pressure information may include FFR or iFR. In some embodiments, the first set of ultrasound information may include information regarding a diameter or cross-sectional profile of the stenotic lesion and/or the first set of pressure information can include information regarding pressure drop across the stenotic lesion.

In some embodiments, the processor may be further adapted to receive additional signals. In some embodiments, the processor may be further adapted to receive a second pressure signal representative of a second intravascular fluid pressure measurement taken near the stenotic lesion. In some preferred embodiments, the processor may be adapted to receive the second pressure signal contemporaneously with the first pressure signal and the first ultrasound signal. In some embodiments, the first set of pressure information may be based on the first intravascular fluid pressure measurement and the second intravascular fluid pressure measurement. In some embodiments, the first intravascular fluid pressure measurement may be taken from a first location that is distal to the stenotic lesion, and the second intravascular fluid pressure measurement may be taken from a second location that is proximal to the stenotic lesion. In some such embodiments, the first set of pressure information can include information regarding pressure drop across the stenotic lesion. In some embodiments, the processor may be further adapted to receive a second ultrasound signal representative of a second intravascular physical dimension measurement taken near the stenotic lesion. In some embodiments, the processor may be further adapted to receive a third ultrasound signal representative of a third intravascular physical dimension measurement taken near the stenotic lesion. In some embodiments, the processor may be adapted to receive the second ultrasound signal and/or the third ultrasound signal contemporaneously with each other and/or with the first pressure signal and the first ultrasound signal. In some embodiments, the first set of ultrasound information may be based on the first intravascular physical dimension measurement, the second intravascular physical dimension measurement, and/or the third intravascular physical dimension measurement. In some embodiments, the first set of ultrasound information may include information regarding a diameter or cross-sectional profile of the vessel lumen adjacent the stenotic lesion. In some embodiments, the second intravascular physical dimension measurement may be taken from a second location that is axially spaced in the vessel lumen from a first location at which the first intravascular physical dimension measurement may be taken. In some embodiments, the control panel may be further adapted to receive from the processor a second set of ultrasound information based the second intravascular physical dimension measurement. In some such embodiments, the control panel may be adapted to display the second set of ultrasound information. In some instances, the first set of ultrasound information may include information regarding a first diameter or a first cross-sectional profile of the vessel lumen at the first location, and the second set of ultrasound information may include information regarding a second diameter or a second cross-sectional profile of the vessel lumen at the second location.

BRIEF DESCRIPTION OF DRAWINGS

The details of one or more examples are set forth in the accompanying drawings and the description below. Other features, objects, and advantages will be apparent from the description and drawings, and from the claims.

FIG. 10A is an illustrative waveform of response signals from two ultrasound transducers with respect to time, with blood being the ultrasound medium.

FIG. 10B is an illustrative waveform of response signals from two ultrasound transducers with respect to time, with a blood displacement fluid being the ultrasound medium.

DETAILED DESCRIPTION

Figure 1:
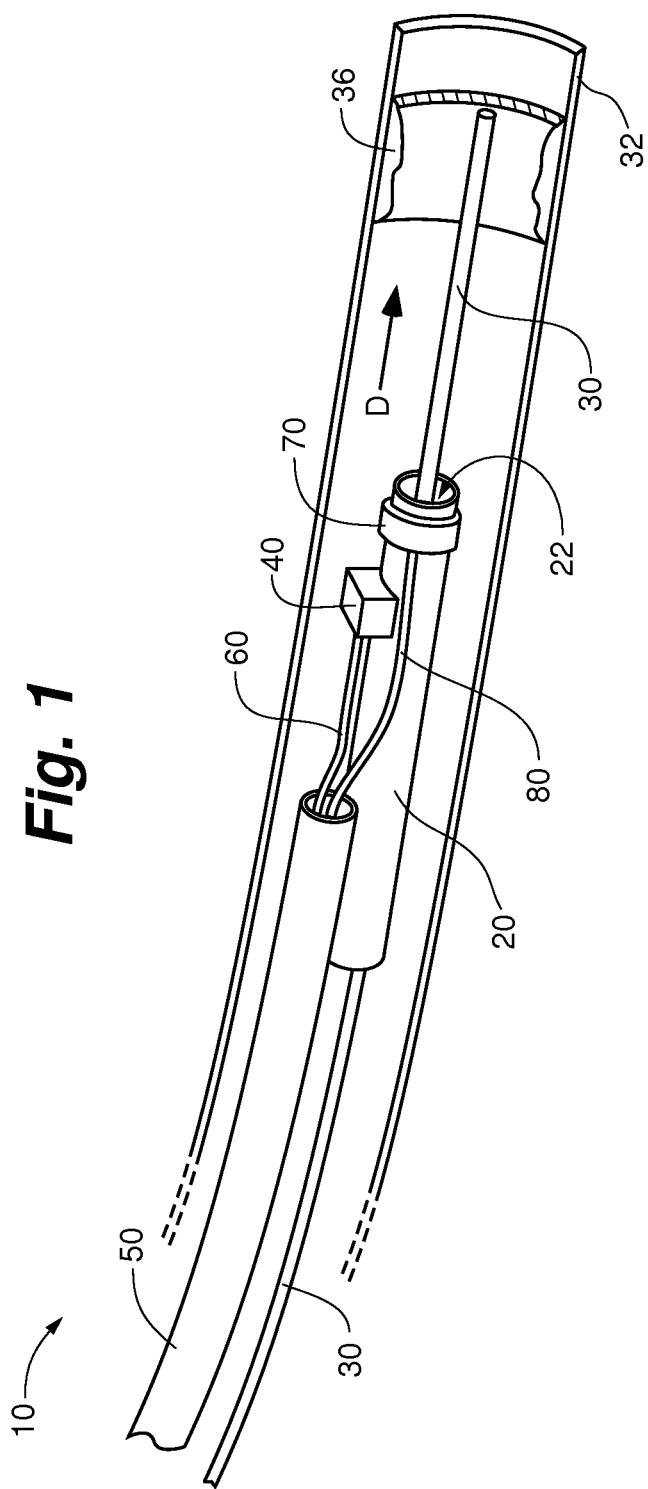
FIG. 1 is a perspective view of a vessel sensing system in accordance with embodiments of the present invention.

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions, and manufacturing processes may be provided for selected elements, and all other elements employ that which is known to those of skill in the field. Those skilled in the art will recognize that many of the examples provided have suitable alternatives that can be utilized.

FIGS. 1-8 show various embodiments of a vessel sensing system 10. The vessel wall 32 is cut away to show the interior of the vessel. Arrow D points in the distal direction, meaning that the direction opposite the arrow D is the proximal direction or the direction that leads outside of the patient's body. As can be seen, FIGS. 1-8 show a stenotic lesion 36 formed in the vessel wall 32.

Embodiments of the vessel sensing system 10 can identify at least two characteristics of the stenotic lesion 36 for purposes of determining whether intervening action should be taken. The vessel sensing system 10 can include a pressure transducer 40 that can be used to determine how the stenotic lesion 36 impacts the pressure of the blood as the blood flows past the stenotic lesion 36. Additionally, embodiments of the vessel sensing system 10 can include an ultrasound transducer (e.g., the ultrasound transducer ring 70 in FIGS. 1, 4 and 7 or the array of individual ultrasound transducers 71 in FIGS. 2, 3, 5, 6 and 8), which can determine, among other things, the interior diameter of the vessel lumen adjacent the stenotic lesion 36 (and/or the cross-sectional area/profile for lesions with a non-circular profile) and the interior diameter of the vessel itself. These characteristics—the pressure drop across the stenotic lesion 36 and the interior diameter of the vessel lumen adjacent the stenotic lesion 36—can provide valuable information to inform a care provider's decision of whether to take intervening action. In some embodiments, one or both of these characteristics can be combined with information provided by an angiogram to aid a care provider in determining whether to have an angioplasty performed, have a stent implanted, etc.

Pressure sensors that can be used in embodiments of the present invention can take a variety of forms. For example, in some embodiments, the pressure transducer 40 may be a fiber optic pressure sensor. An example of a fiber optic pressure sensor is a Fabry-Perot fiber optic pressure sensor, which is a commercially available sensor. Examples of Fabry-Perot fiber optic sensors are the "OPP-M" MEMS-based fiber optic pressure sensor (400 micron size) manufactured by Opsens (Quebec, Canada), and the "FOP-MIV" sensor (515 micron size) manufactured by Fiso Technologies, Inc. (Quebec, Canada). In embodiments of the invention using the Fabry-Perot fiber optic pressure sensor as the pressure transducer 40, such a transducer works by having a reflective diaphragm that varies a cavity length measurement according to the pressure against the diaphragm. Coherent light from a light source travels down the fiber and crosses a small cavity at the sensor end. The reflective diaphragm reflects a portion of the light signal back into the fiber. The reflected light travels back through the fiber to a detector at the light source end of the fiber. The two light waves, the source light and reflected light travel in opposite directions and interfere with each other. The interference pattern will vary depending on the cavity length. The cavity length will change as the diaphragm deflects under pressure. The interference pattern is registered by a fringe pattern detector. In some embodiments, the pressure transducer 40 may be a piezo-resistive pressure sensor (e.g., a MEMS piezo-resistive pressure sensor). In some embodiments, the pressure transducer 40 may be a capacitive pressure sensor (e.g., a MEMS capacitive pressure sensor). A pressure sensing range from about −50 mm Hg to about +300 mm Hg (relative to atmospheric pressure) may be desired for making many physiological measurements with the pressure transducer 40.

In some embodiments, multiple pressure sensors can be spaced axially in the vessel lumen from one another. For example, two, three, four, five, six or more pressure transducers may be spaced apart from one another by equal or unequal distances. In some embodiments, the distance between the multiple pressure transducers may be variable. More detail in this regard is provided elsewhere herein (see, e.g., FIG. 9 and the corresponding discussion).

Ultrasound transducer(s) 70, 71 used in connection with embodiments of the vessel sensing system 10 can have a variety of characteristics. Commonly, ultrasound transducers comprise piezoelectric crystals that deform in response to electrical signals at predetermined frequencies. The frequency at which a crystal deforms depends on how the crystal is manufactured. When the crystals deform at ultrasonic frequencies, they emit ultrasound energy. In intravascular ultrasound applications, the crystals are commonly positioned generally axially so that the ultrasound energy propagates through the blood (or other fluid) in a generally radial direction. The ultrasound energy is then partly reflected back to the crystal, which is again deformed in a manner that generates an electrical return signal that can be provided to processing equipment for processing. How the crystal is manufactured can also impact the frequency at which the crystal can respond. Higher frequency ultrasound energy (e.g., greater than 50 MHz) can provide resolution that is very good, but differentiation between the blood (or other fluid) and the vessel wall 32 is not as good. In contrast, lower frequency ultrasound energy can provide differentiation that is very good but resolution that is not as good. The ultrasound transducer can be an ultrasound transducer ring 70 that emits ultrasound energy roughly uniformly in all radial directions. In some embodiments, multiple individual ultrasound transducers 71 may be arranged to form a ring so as to emit ultrasound energy in specific radial directions. For example, in some embodiments three individual ultrasound transducers 71 may be spaced evenly about a circumference, thereby emitting ultrasound energy in radial directions 120 degrees spaced apart from each other. Larger or smaller numbers of individual ultrasound transducers 71 (e.g., 2, 3, 4, 5, 6, 7, or more) may be used, and the spacing between them may be even or uneven. In another example, multiple individual ultrasound transducers 71 may be spaced about a circumference and the phase of the signal may be controlled in order to focus the resulting ultrasonic wave. The focusing position can be varied substantially continuously in order to discern the peak.

Determining the diameter or cross-sectional area/profile of the vessel lumen adjacent a stenotic lesion can be valuable for characterizing the lesion. In some instances, the diameter or cross-sectional area/profile can be used to assess how much impact the stenotic lesion has on the patient's physiology. In some instances, the diameter or cross-sectional area/profile can be used to correct errors in FFR calculations based on objects being in the vessel lumen adjacent the lesion. In some instances, the diameter or cross-sectional area/profile can be used to choose an appropriate stent with more confidence than if the diameter or cross-sectional area/profile had been estimated via an angiogram. In some instances, the diameter or cross-sectional area/profile can be used after stent deployment to determine whether the stent is fully deployed.

In some embodiments, transducers for measuring other physiological parameters of a patient can be used. For example, some embodiments incorporate a transducer for measuring a blood parameter, such as blood temperature, blood pH, blood oxygen saturation levels, and so on. The transducer may be configured to then generate a signal representative of the physiological parameter. Such transducer(s) may be used to supplement the pressure transducer(s) and/or the ultrasound transducer(s), or such transducer(s) may be used in place of the pressure transducer(s) and/or the ultrasound transducer(s). Information provided by such transducer(s) can be used to further characterize a stenotic lesion and/or for other purposes.

Embodiments of the vessel sensing system 10 include specific structure for delivering the ultrasound transducer(s) 70, 71 and the pressure transducer 40 to the stenotic lesion 36. In some embodiments, that specific structure includes a distal sleeve 20 coupled to a proximal portion 50. The distal sleeve 20 can include a guidewire lumen 22 through which a guidewire 30 may pass. In this way, a guidewire 30 may first be delivered to the area of interest (e.g., an area that includes the stenotic lesion) and the proximal end of the guidewire 30 (i.e., the end that is outside of the patient's body) may be inserted into the guidewire lumen 22 of the distal sleeve 20 such that the distal sleeve 20 may be guided along the guidewire 30 to the area of interest. With the proximal portion being coupled to the distal sleeve 20, the proximal portion 50 may likewise be delivered to the area of interest via the guidewire 30.

In FIGS. 1-9, conductor 60 is shown as being connected to pressure transducer 40, and various conductors 80, 81, 82 are shown as being connected to ultrasound transducers 70, 71. Examples of conductors include coaxial cable, twisted pair cable, etc. Electrical signals, as discussed elsewhere herein, are transmitted to and from the transducers via the respective conductors. As shown, the conductors 60, 80, 81, 82 extend within one or more lumens of the proximal portion 50. In practice, the conductors 60, 80, 81, 82 are typically not exposed to the blood (or blood displacement fluid) flowing through the vessel lumen. In some configurations, a cover can be wrapped around distal sheath 20 to isolate the conductors 60, 80, 81, 82 from the vessel lumen. In some configurations, one or more conductors 60, 80, 81, 82 may be embedded into the distal sheath 20. Electrical impedance of the conductors 60, 80, 81, 82 can be designed/selected to match that of the respective transducer 40, 70, 71 (typically between 10 ohms and 100 ohms). In some instances, the conductors 60, 80, 81, 82 may be designed/selected to minimize loss of the electrical signal travels to and from the respective transducers 40, 70, 71 (e.g., 1-2 dB). In many instances, the diameter of each of the conductors 60, 80, 81, 82 may be minimized (in the context of other design constraints) to minimize any degradation of catheter deliverability due to added stiffness of any of the conductors 60, 80, 81, 82.

As can be seen, the axial length of the distal sleeve 20 is relatively small in comparison with the length of the guidewire 30, which extends proximally from the area of interest that includes the stenotic lesion 36 all the way back proximally out of the patient's body. This can provide significant advantages over catheters that extend over the guidewire 30 from outside of the patient's body all the way into the area of interest. For example, once the guidewire 30 has been advanced all the way into the area of interest, it can be quite beneficial to leave it there and not retract it until dictated by the medical procedure. On the other hand, it may be desirable to introduce the vessel sensing system 10 into the patient's vessel, take relevant measurements, remove the vessel sensing system 10, and use the guidewire 30 for other purposes (e.g., delivering a stent to the stenotic lesion 36). If the pressure transducer 40 and the ultrasound transducer(s) 70, 71 were delivered by a catheter that extended from the area of interest all the way outside of the patient's body, it would be very difficult to remove that catheter from the patient's body while maintaining the position of the guidewire 30. In contrast, a vessel sensing system 10 with a distal sleeve 20 having a relatively short axial length may be removed from the patient's body while holding the guidewire 30 in place. Additional detail about the advantages of using such a distal sleeve 20 can be found in commonly assigned U.S. patent application Ser. No. 12/557,685 ("Physiological Sensor Delivery Device and Method"), which is hereby incorporated by reference herein in its entirety.

Figure 2:
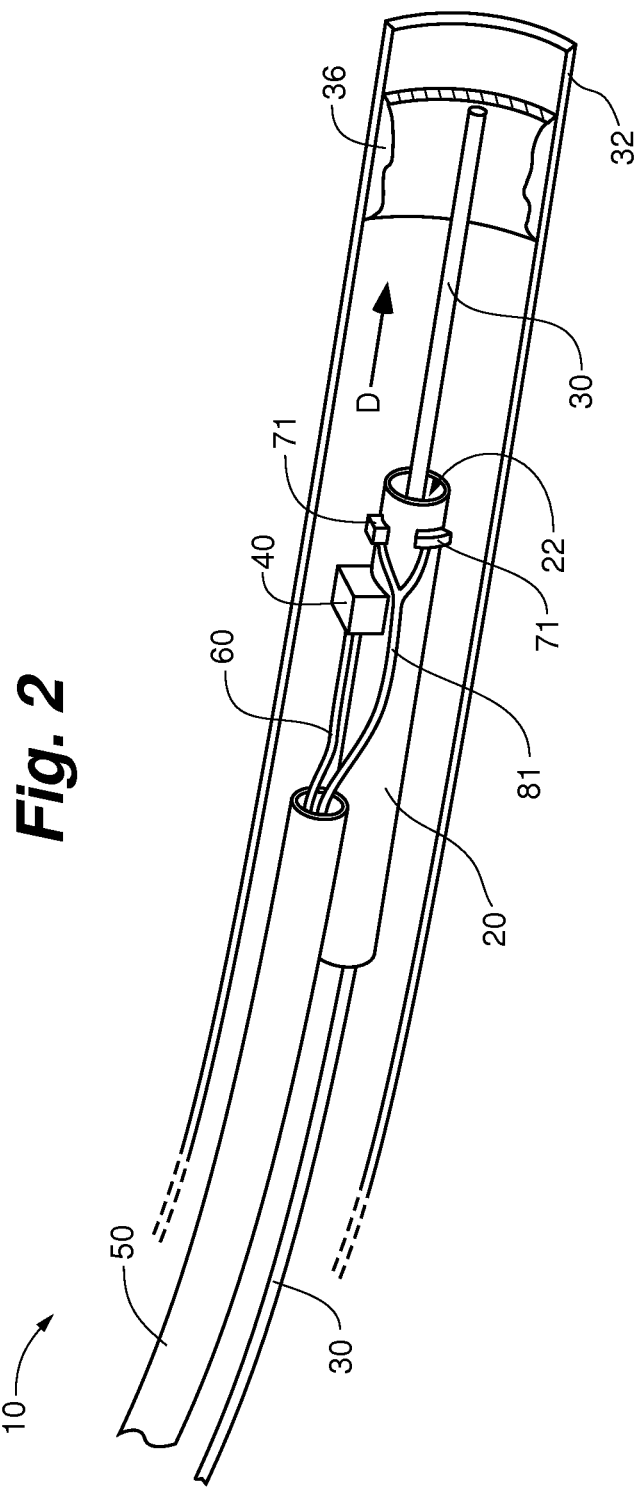
FIG. 2 is a perspective view of a vessel sensing system in accordance with embodiments of the present invention.
Figure 3:
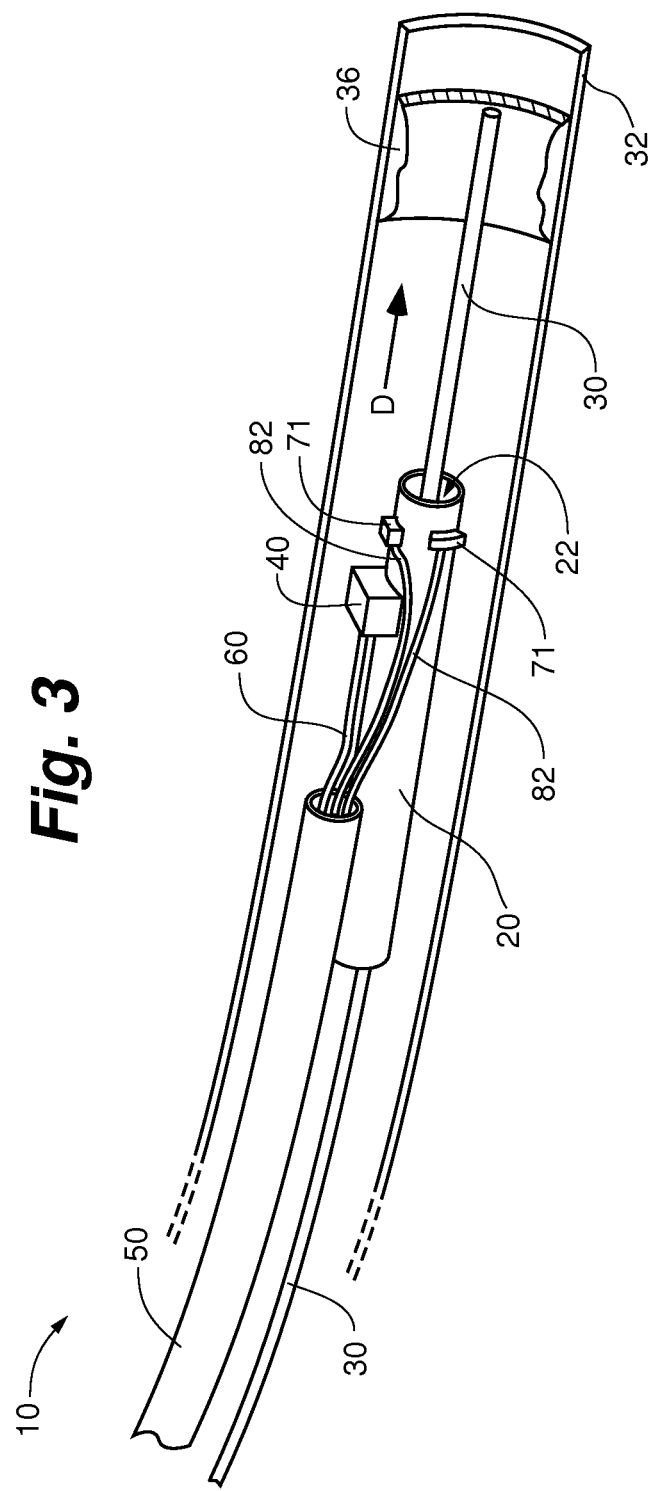
FIG. 3 is a perspective view of a vessel sensing system in accordance with embodiments of the present invention.
Figure 4:
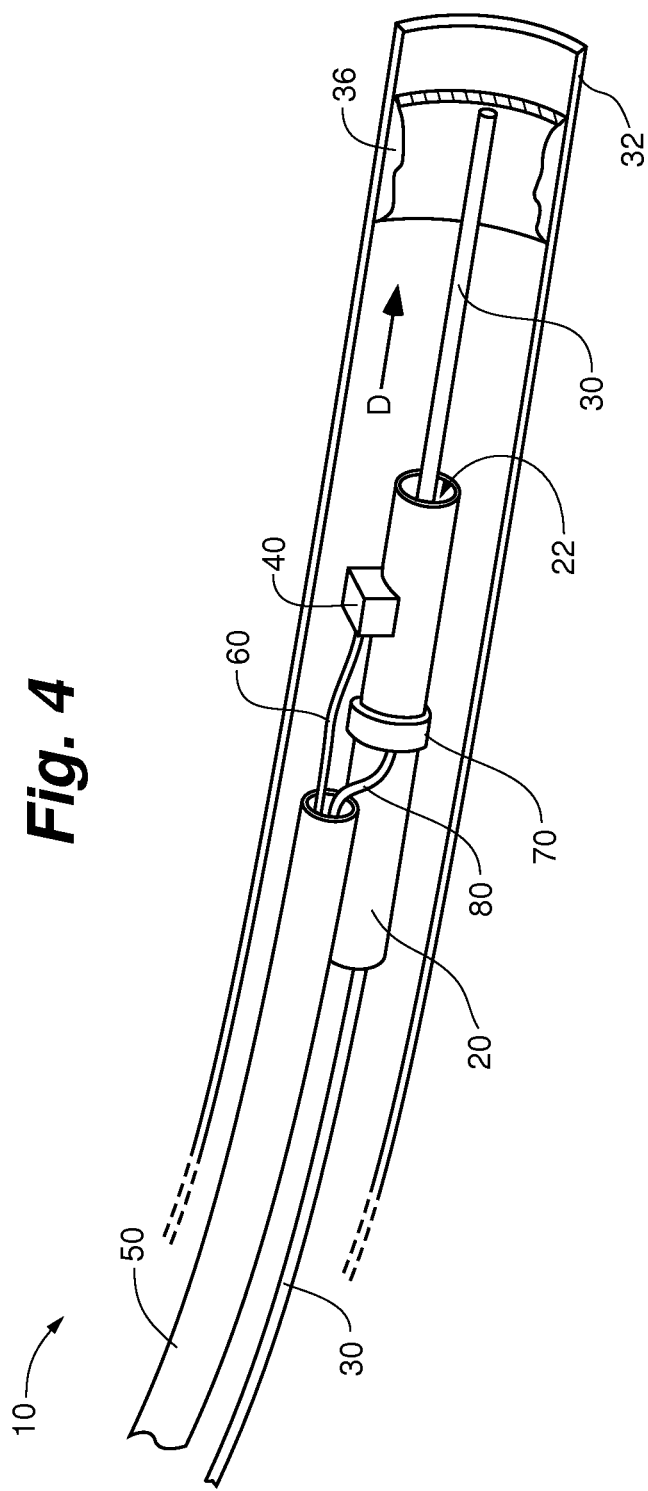
FIG. 4 is a perspective view of a vessel sensing system in accordance with embodiments of the present invention.
Figure 5:
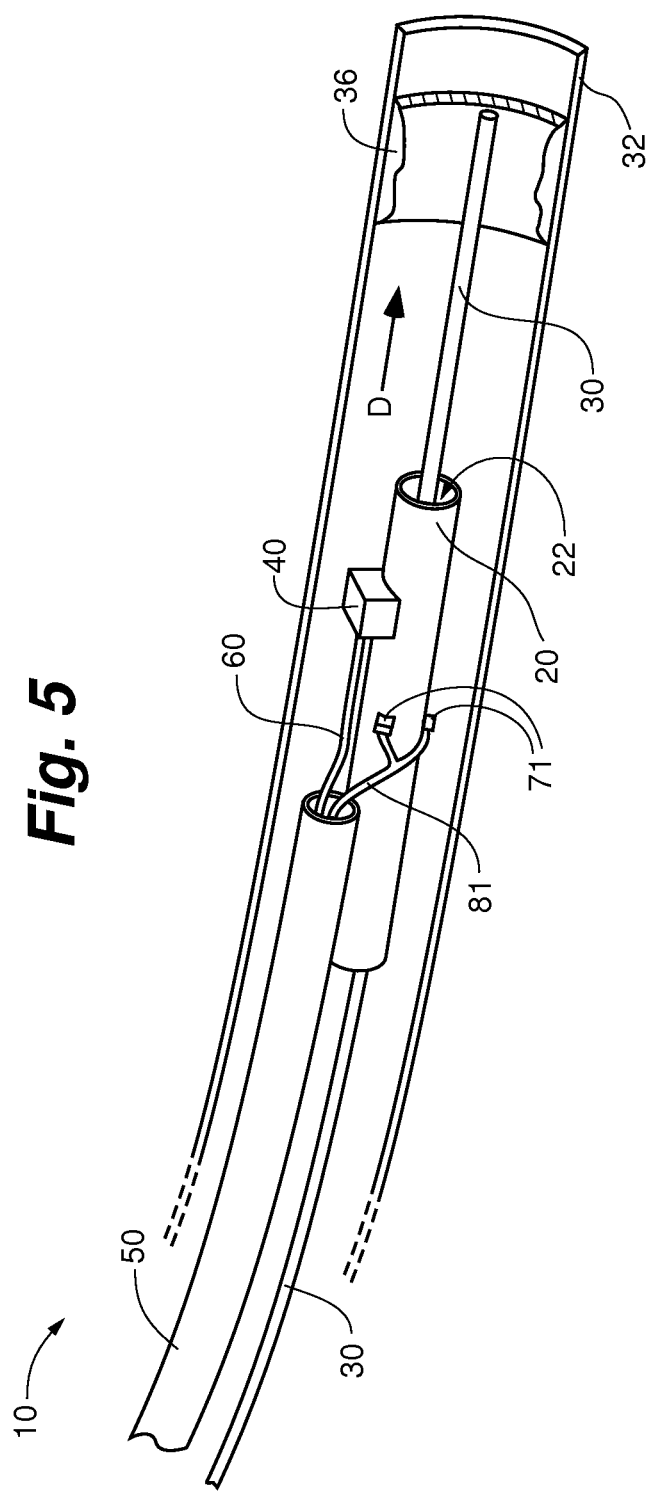
FIG. 5 is a perspective view of a vessel sensing system in accordance with embodiments of the present invention.
Figure 6:
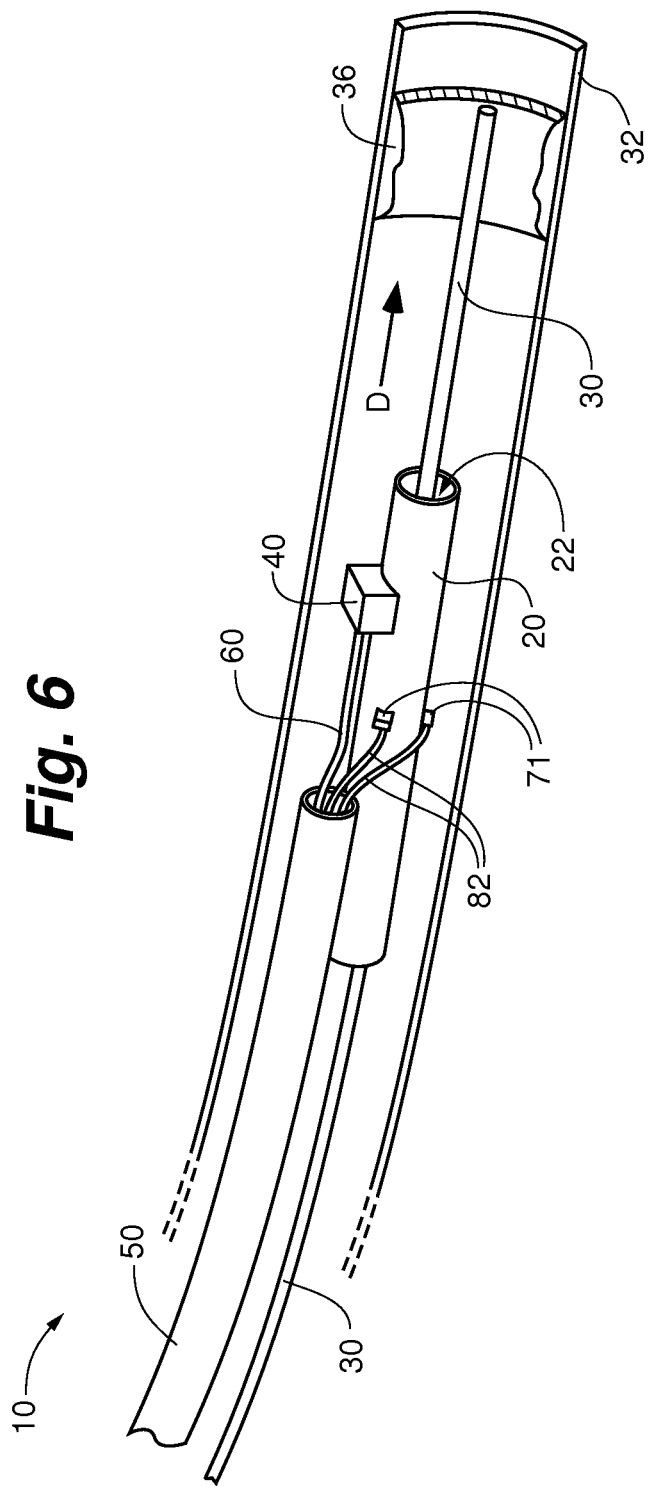
FIG. 6 is a perspective view of a vessel sensing system in accordance with embodiments of the present invention.
Figure 7:
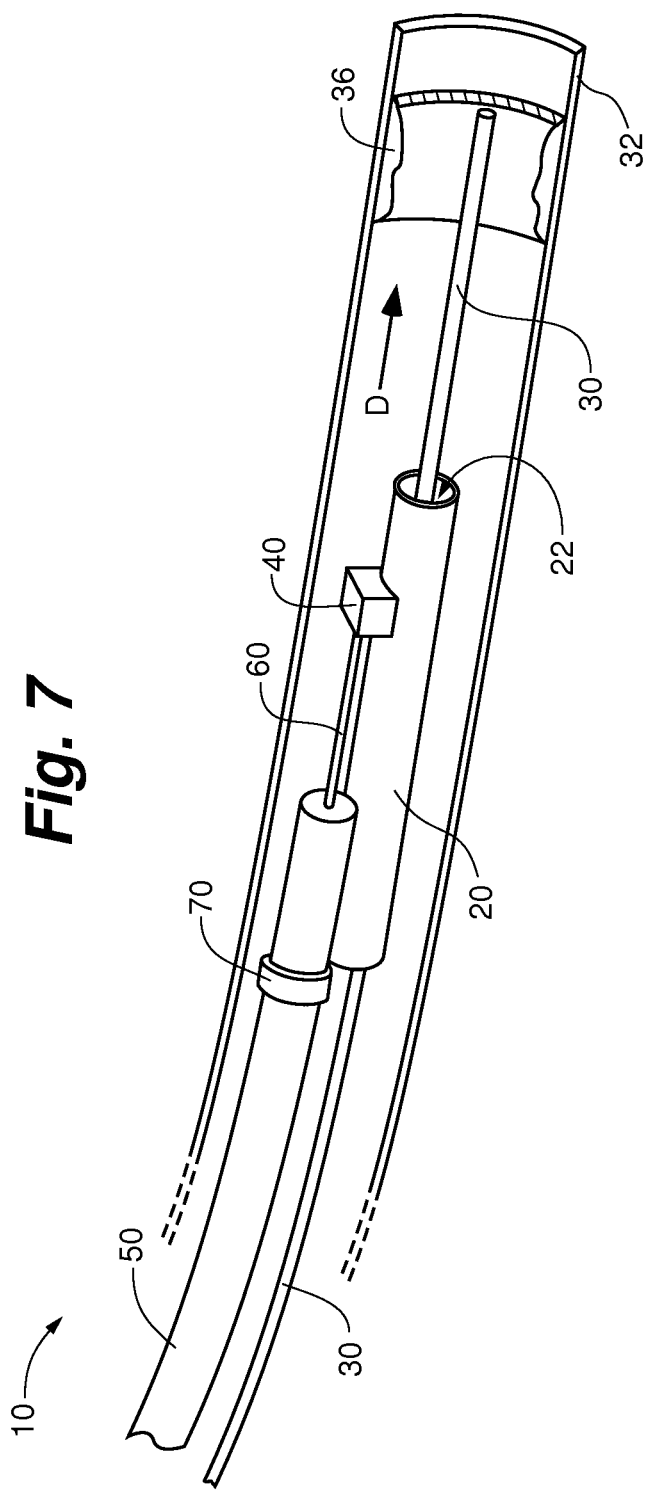
FIG. 7 is a perspective view of a vessel sensing system in accordance with embodiments of the present invention.
Figure 8:
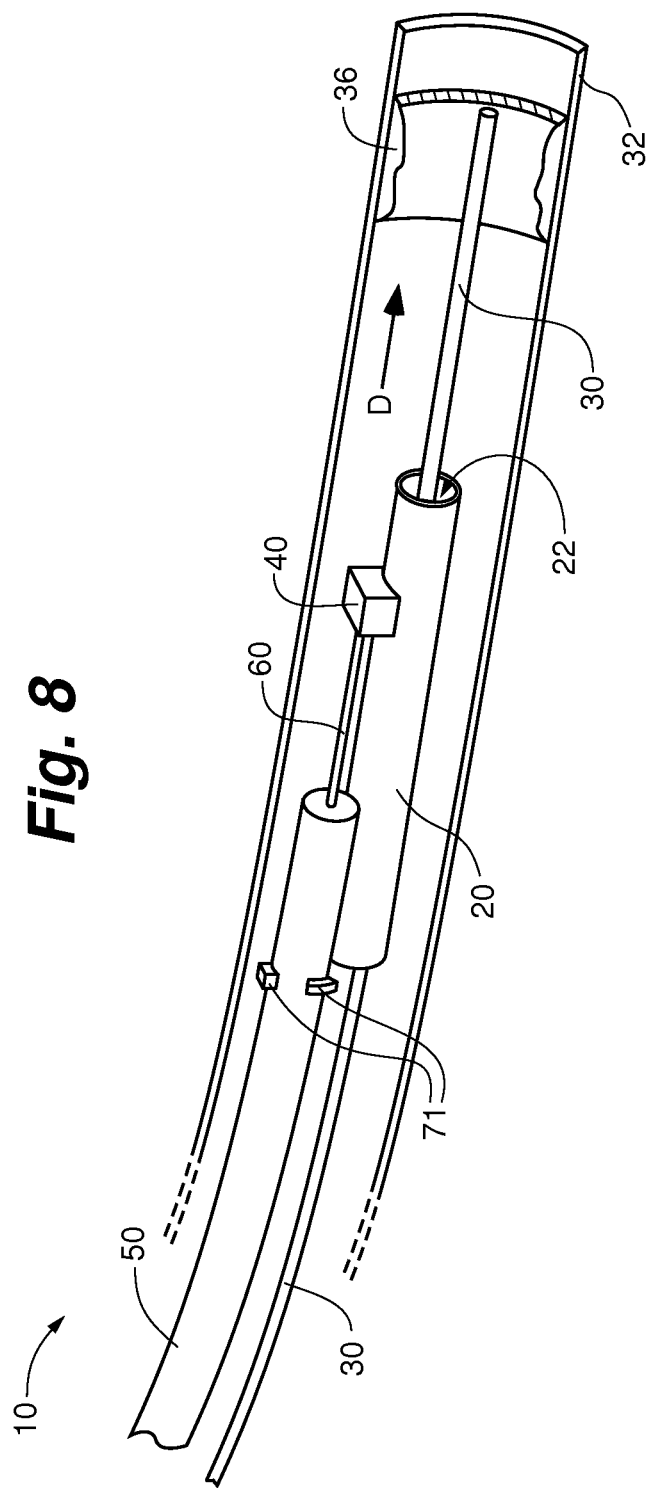
FIG. 8 is a perspective view of a vessel sensing system in accordance with embodiments of the present invention.

The pressure transducer 40 and the ultrasound transducer(s) 70, 71 can be positioned in various locations in vessel sensing system 10. FIGS. 1, 2 and 3 show the ultrasound transducer(s) 70, 71 coupled to the distal sleeve 20 distal of the pressure transducer 40. FIGS. 4, 5 and 6 show the ultrasound transducer(s) 70, 71 coupled to the distal sleeve 20 proximal of the pressure transducer 40. FIGS. 7 and 8 show the ultrasound transducer(s) 70, 71 coupled to the proximal portion 50. While the figures show the pressure transducer 40 coupled to the distal sleeve 20 in a similar location, the pressure transducer 40 may be located more proximal or more distal on the distal sleeve 20 or on the proximal portion 50. In some embodiments, the pressure transducer 40 and/or the ultrasound transducer(s) 70, 71 can be spaced in various positions about the circumference of the distal sleeve 20 and/or the proximal portion 50. As noted elsewhere herein, multiple pressure transducers can be provided—spaced axially in the vessel lumen from one another and/or about the circumference of the distal sleeve 20 and/or the proximal portion 50. In some embodiments, multiple ultrasound transducers (and/or sets of ultrasound transducers) may be spaced axially in the vessel lumen apart from one another along the distal sleeve 20 and/or the proximal portion 50. Many other variations are contemplated, depending on the particular application.

In use, the pressure transducer 40 can be used to measure the pressure drop across the stenotic lesion 36. A technique for evaluating the degree to which a stenotic lesion 36 obstructs flow through a blood vessel is called the Fractional Flow Reserve measurement (FFR). To calculate the FFR for a given stenotic lesion, two blood pressure readings are taken—one on the distal side of the stenosis (e.g., downstream from the stenosis), the other pressure reading is taken on the proximal side of the stenosis (e.g., upstream from the stenosis, towards the aorta). The FFR is defined as the ratio of maximal blood flow in a stenotic artery, taken distal to the lesion, to normal maximal flow, and is typically calculated based on a measured pressure gradient of the distal pressure (less the venous pressure) to the proximal pressure (less the venous pressure). The FFR is therefore a unitless ratio of the distal and proximal pressures. The pressure gradient, or pressure drop, across a stenotic lesion is an indicator of the severity of the stenosis, and the FFR is a useful tool in assessing the pressure drop. The more restrictive the stenosis is, the greater the pressure drop, and the lower the resulting FFR. The FFR measurement may be a useful diagnostic tool. For example, clinical studies have shown that an FFR of less than about 0.75 may be a useful criterion on which to base certain therapy decisions. Pijls, DeBruyne et al., Measurement of Fractional Flow Reserve to Assess the Functional Severity of Coronary-Artery Stenoses, 334: 1703-1708, New England Journal of Medicine, Jun. 27, 1996. A physician might decide, for example, to perform an interventional procedure (e.g., angioplasty or stent placement) when the FFR for a given stenotic lesion is below 0.75, and may decide to forego such treatment for lesions where the FFR is above 0.75. More detail regarding FFR can be found in commonly assigned U.S. patent application Ser. No. 12/557,685 ("Physiological Sensor Delivery Device and Method") which is incorporated by reference above.

In some instances, FFR can be adjusted to account for the presence of delivery equipment in the vessel lumen adjacent the stenotic lesion 36. For example, when the distal sleeve 20 carries the pressure transducer 40 past the stenotic lesion 36 to a distal position, part of the distal sleeve 20 itself may remain in the narrowed vessel lumen defined by the stenotic lesion 36. This may introduce error due to the cross sectional size of the distal sleeve 20 and the guidewire 30. As the distal sleeve 20 and the guidewire 30 cross the lesion, they introduce blockage, in addition to that caused by the lesion itself. The measured distal pressure would therefore be somewhat lower than it would be without the additional flow obstruction, which may exaggerate the measured pressure gradient across the lesion. Methods of correcting for such error are taught in commonly assigned U.S. patent application Ser. No. 13/469,485 ("Intravascular Sensing Method and System"), which is hereby incorporated by reference herein in its entirety. In some embodiments, additional information regarding the stenotic lesion 36 gathered through means discussed herein may be used to enhance correction of FFR error.

In many instances, pressure measurements used for purposes of calculating a patient's FFR are taken when the patient is under hyperemic conditions. To cause the hyperemic conditions in the patient, adenosine (or other vasodilatory drug) is commonly administered to the patient. The adenosine gets into the patient's downstream circulation and causes vasodilation, opening up the downstream vessels. This can minimize the variability in the downstream resistance to blood flow, thereby making the FFR ratio more representative of the pressure drop caused by the stenotic lesion. Minimizing the variability in the downstream blood flow can also have the effect of "standardizing" FFR ratios, making them more readily comparable with other FFR ratios taken under hyperemic conditions.

In some instances, administering a vasodilatory drug like adenosine to a patient can have drawbacks. It can add a significant amount of extra setup time, which can have a detrimental effect on efficiency. In some instances, vasodilatory drugs can cause discomfort to some patients. For these and other reasons, some care providers prefer to avoid administering vasodilatory drugs to patients when assessing the severity of stenotic lesions.

A recent study proposed a method of measuring pressure drop across a stenotic lesion without using vasodilatory drugs. This method, called the instantaneous wave-Free Ratio (iFR), relies on a short segment of the coronary waveform in which the downstream resistance to blood flow is relatively stable. The proximal and distal values on that segment of the coronary waveform are compared to one another to form a ratio that, like FFR, provides information regarding the pressure drop across the stenosis, which can aid care providers in deciding whether interventional action (e.g., a stent or angioplasty) is warranted.

Figure 9:
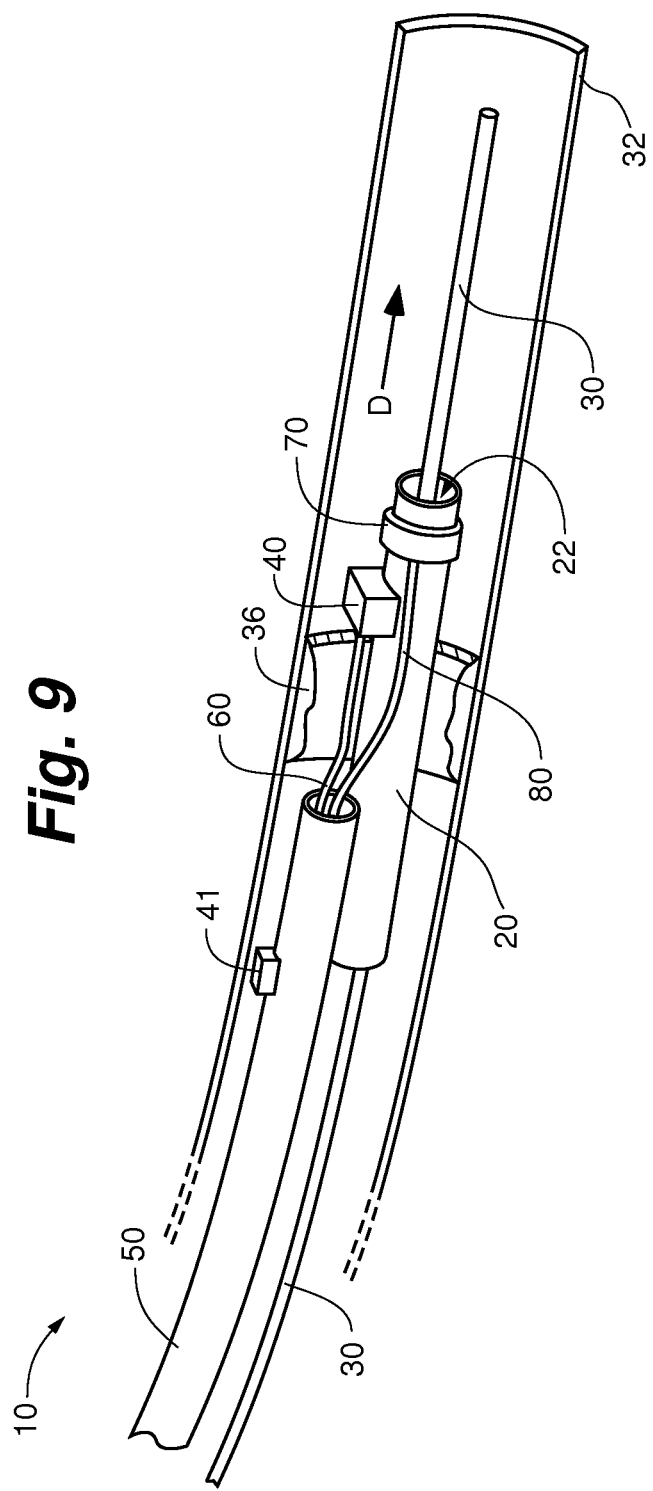
FIG. 9 is a perspective view of a vessel sensing system in accordance with embodiments of the present invention.

FIG. 9 shows a vessel sensing system 10 with multiple pressure transducers 40, 41 spaced axially from one another in the vessel lumen. In some embodiments, the pressure transducers 40, 41 can be positioned both on the proximal portion 50, both on the distal sleeve 20, one on the proximal portion 50 and one on the distal sleeve 20, and so on. Embodiments with multiple pressure transducers 40, 41 can be advantageous in measuring both FFR and iFR. In both FFR and iFR, a pressure transducer 40 can be positioned distal to the stenotic lesion 36 and can provide distal pressure measurements to processing equipment via a pressure transducer conductor 60. For measuring pressure proximal to the stenotic lesion 36, a second pressure transducer 41 can be positioned proximal to the stenotic lesion 36 and can provide proximal pressure measurements to processing equipment via a pressure transducer conductor. In some instances, proximal pressure may be measured more accurately and reliably via an invasive pressure transducer, like the second pressure transducer 41, than via an external pressure transducer that measures proximal pressure through the fluid within a guide catheter physically coupled to the external pressure transducer. This is because the shape of the waveform can be influenced by "ringing" and "damping" effects of the guide catheter, the fluid within the guide catheter, and the external transducer. The increased accuracy and reliability provided by an invasive pressure transducer can be especially beneficial for procedures that do not involve vasodilatory drugs (e.g., iFR) because they are typically based on a pressure value taken at a particular segment of the coronary waveform, whereas FFR typically uses only the mean proximal pressure.

Referring again to FIGS. 1-9, the ultrasound transducer(s) 70, 71 can be used to determine the interior diameter (or cross-sectional area, e.g., for non-circular stenotic lesions) of the vessel lumen adjacent the stenotic lesion 36. In some embodiments, the ultrasound transducer(s) 70, 71 can be used to determine the interior diameter across the entire axial profile of the stenotic lesion 36. The ultrasound transducer(s) 70, 71 can determine the interior diameter of the vessel lumen adjacent the stenotic lesion 36 across the lesion's entire axial profile by emitting and receiving ultrasound energy as they are moved axially in the vessel lumen from one side of the stenotic lesion 36 to the other. In some embodiments, the proximal portion 50, and thus the distal sleeve 20, may be rotated (e.g., manually) during translation of the ultrasound transducer(s) 70, 71 across the lesion's axial profile (e.g., during pullback of the proximal portion 50). In some such embodiments, the rotational position can be correlated with the ultrasound signals emitted/received. Some such embodiments can be used to provide dimensional information at a variety of rotational positions, which can lead to an effective characterization of the vessel lumen adjacent the stenotic lesion 36. The ultrasound transducer(s) 70, 71 can be manufactured to emit ultrasound energy in response to a stimulus signal at a predetermined frequency. The type of ultrasound energy emitted by the ultrasound transducer(s) 70, 71 can be calibrated to clearly differentiate between fluid flowing in the vessel (e.g., blood, a blood displacement fluid such as saline, etc.) and the vessel wall 32. Ultrasound energy emitted at higher frequencies provides greater resolution but less differentiation between the vessel fluid and the vessel wall 32, whereas ultrasound energy emitted at lower frequencies provides better differentiation between vessel fluid and vessel wall 32 but not as good resolution. In many instances, when desiring the interior diameter of the vessel lumen adjacent the stenotic lesion 36 and not an entire image of the stenotic lesion 36, strong differentiation can be of more importance than high resolution. Embodiments in which the pressure transducer(s) 40, 41 comprise a fiber optic sensor may be advantageous in that high frequency ultrasound energy and/or RF electrical noise can have minimal effect on the operation of the fiber optic sensors.

In some instances, it may be advantageous to compare interior diameter calculations obtained by propagating ultrasound energy through a first fluid with interior diameter calculations obtained by propagating ultrasound energy through a second fluid. For example, a first set of interior diameter calculations can be obtained by propagating ultrasound energy through blood flowing through the patient's vessel, and a second set of interior diameter calculations can be obtained by propagating ultrasound energy through a blood displacement fluid (e.g., saline) flowing through the patient's vessel. The first and second sets of interior diameter calculations can be compared to one another to obtain more reliable measurements. FIGS. 10A-10B provide illustrative waveforms, with FIG. 10A showing the response signal through blood and FIG. 10B showing the response signal through a blood displacement fluid. The first peak in each response signal, T1B and T1S, can correspond to the inner wall of the lesion, and the second peak in each response signal, T2B and T2S, can correspond to the vessel's outer wall. The difference between T1B and T0 will not match the difference between T1S and T0 because ultrasound energy travels at different rates between the two fluids. On the other hand, the difference between T2B and T1B should match the difference between T2S and T1S because the ultrasound energy is reflecting from the lesion and vessel wall during both time periods. This relationship can make it easier to identify the first peak, which can then be used to determine the distance between the ultrasound transmitter and the inner wall and the lesion.

Referring again to FIGS. 1-9, in embodiments that use an ultrasound transducer ring 70, a single stimulus signal can be provided to the ultrasound transducer ring 70 by way of a single ultrasound transducer conductor 80. The ultrasound transducer ring 70 can emit ultrasound energy roughly uniformly in all radial directions. The ultrasound transducer ring 70 can create an electrical signal based on the ultrasound energy reflected back to it and can transmit that electrical signal through ultrasound transducer conductor 80. That electrical signal can then be used to determine the interior diameter of the vessel lumen adjacent the stenotic lesion 36. The process of transmitting and receiving ultrasound energy by the ultrasound transducer ring 70 can be performed multiple times at multiple points as the ultrasound transducer ring 70 is moved axially in the vessel lumen across the stenotic lesion 36. Similarly, the individual ultrasound transducers 71 can receive a stimulus signal either from a common conductor 81 or from separate individual conductors 82. In some embodiments, the individual ultrasound transducers 71 may be configured to begin emitting ultrasound energy upon receiving a stimulus signal of approximately the same frequency. In some embodiments, the individual ultrasound transducers 71 may be configured to begin emitting ultrasound energy in response to stimulus signals at different frequencies. For example, a stimulus frequency may be varied over time causing (a) a first ultrasound transducer 71 to begin emitting ultrasound energy at a first time and a first frequency, (b) a second ultrasound transducer 71 to begin emitting ultrasound energy at a second time and a second frequency, and (c) a third ultrasound transducer 71 to begin emitting ultrasound energy at a third time and a third frequency. In some embodiments, multiple individual ultrasound transducers may be electrically tied together (e.g., a single coaxial conductor connecting with three ultrasound transducers). In some such embodiments, a very broadband signal (e.g., a short-time pulse or a broadband chirp) can be provided as a stimulus signal, which can excite only those frequencies to which the individual ultrasound transducers are sensitive. When the individual ultrasound transducers 71 receive ultrasound energy, they convert the received ultrasound energy to an electrical signal and transmit the electrical signals via the common conductor 81 or the individual conductors 82, depending on the particular embodiment.

Figure 14:
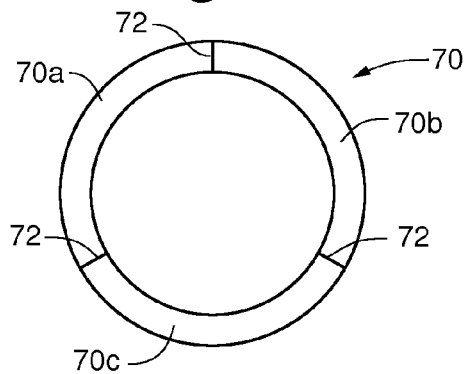
FIG. 14 is a schematic end view of an illustrative ultrasound transducer ring used in connection with embodiments of the present invention.
Figure 15:
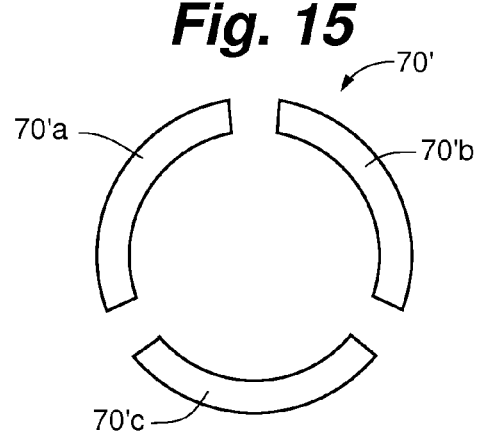
FIG. 15 is a schematic end view of an illustrative ultrasound transducer ring used in connection with embodiments of the present invention.
Figure 16A:
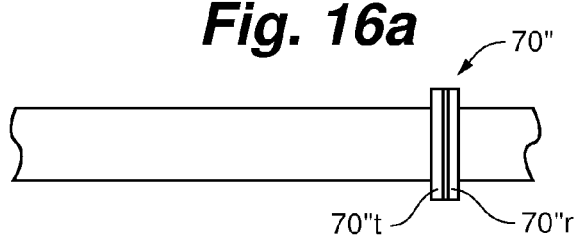
FIG. 16a is a schematic side view of a distal sheath with an illustrative ultrasound transducer ring used in connection with embodiments of the present invention.
Figure 16B:
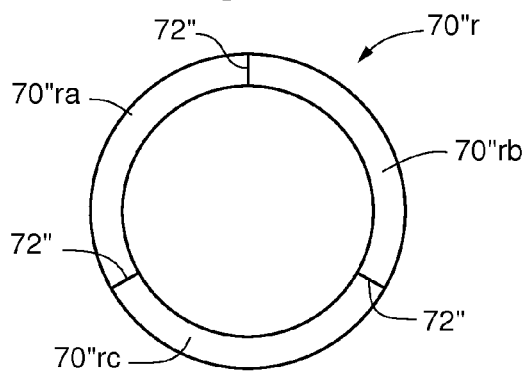
FIG. 16b is a schematic end view of an illustrative ultrasound receiver ring used in connection with embodiments of the present invention.
Figure 16C:
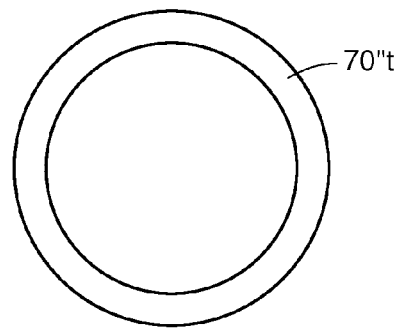
FIG. 16c is a schematic end view of an illustrative ultrasound transmitter ring used in connection with embodiments of the present invention.

FIGS. 14, 15, and 16a-16b provide illustrative ultrasound transducer ring embodiments. FIG. 14 shows an ultrasound transducer ring 70 with ring transducer elements 70a, 70b, 70c, which may operate at a nominal center frequency between 10 MHz and 80 MHz, more typically between 20 MHz and 60 MHz. The ring transducer elements 70a, 70b, 70c may be mechanically separated by kerfs 72 to inhibit mechanical cross-talk between the ring transducer elements 70a, 70b, 70c. FIG. 15 shows a segmented ring transducer 70' that includes three transducer elements 70'a, 70'b, 70'c. The size of the segmented ring transducer elements 70'a, 70'b, 70'c may be optimized to balance sensitivity and spatial resolution, which may depend in part on transducer aperture size. In some embodiments, the transducer elements 70'a, 70'b, 70'c may operate at a nominal center frequency between 10 MHz and 80 MHz, more typically between 20 MHz and 60 MHz. In some embodiments, each of the transducer elements 70'a, 70'b, 70'c may operate at different nominal center frequencies between 10 MHz and 80 MHz, more typically between 20 MHz and 60 MHz. An advantage of segmented ring transducer elements 70'a, 70'b, 70'c operating at different frequencies is the ability to detect only specific signal frequencies which may in turn facilitate physical dimension measurements. The transducer ring 70 and segmented ring transducer 70' of FIGS. 14 and 15, respectively, may operator as both a transmitter and a receiver. FIG. 16a shows still another embodiment of an ultrasound transducer 70" that includes a separate transmitter 70"t and receiver 70"r. FIG. 16c shows a single-element ring transducer 70"t that may operate at a nominal center frequency between 10 MHz and 80 MHz, more typically between 20 MHz and 60 MHz. FIG. 16b shows a ring transducer 70"r that includes three transducer elements 70"ra, 70"rb, 70"rc. The transducer 70" of FIGS. 16a, 16b, 16c that includes a separate transmitter 70"t and receiver 70"r may enable a simpler ultrasound transmitter while preserving improved spatial resolution of a multiple element receiver transducer.

The relative locations of the ultrasound transducer(s) 70, 71 and the pressure transducer 40 can impact the accuracy of the interior diameter and pressure drop measurements. In many embodiments, pressure drop is measured by positioning the pressure transducer 40 distal of the stenotic lesion 36. Proximal pressure can be measured either by fluid pressure taken proximal of the vessel sensing system 10 (e.g., aortic pressure) or by a second pressure transducer coupled, for example, to the proximal portion 50 (see FIG. 9). Measuring pressure distal of the stenotic lesion 36 can be impacted by other objects within the vessel lumen adjacent the stenotic lesion 36 such as the distal sleeve 20, the proximal portion 50, etc. It can be desirable to avoid positioning the ultrasound transducer 70, 71 within the stenotic lesion 36 while the pressure transducer 40 is measuring pressure distal of the stenotic lesion 36. Thus, embodiments in which the ultrasound transducer(s) 70, 71 are positioned distal to the pressure transducer 40 (e.g., FIGS. 1-3) may result in fewer objects being in the vessel lumen adjacent the stenotic lesion 36 during measurement of distal pressure, thereby reducing the error caused by having objects within the vessel lumen adjacent the stenotic lesion 36. In some instances, the vessel diameter distal to the stenotic lesion 36 may decrease substantially in a short distance. In such instances, having the ultrasound transducer(s) 70, 71 positioned distal to the pressure transducer 40 may impede the distal sleeve 20 from moving far enough distally to properly position the pressure transducer 40. In such cases, having the ultrasound transducer(s) 70, 71 positioned proximal to the pressure transducer 40 may be desirable (though moving the ultrasound transducer(s) 70, 71 completely across the stenotic lesion 36 may likewise be impeded by the distal pressure transducer 40). In many embodiments, it may be desirable to position the ultrasound transducer(s) 70, 71 relatively close axially to the pressure transducer 40.

The desire to keep the vessel lumen adjacent the stenotic lesion 36 relatively free from objects when measuring distal pressure may also impact whether individual conductors 82 or a common conductor 81 are used to connect to the individual ultrasound transducers 71. Each ultrasound conductor 81, 82 can include a stimulus lead and a reference or ground lead. If there are three individual ultrasound transducers 71 positioned about the circumference of the distal sleeve 20, and each individual ultrasound transducer 71 is connected to a common ultrasound conductor 81, that would result in six leads (two per individual ultrasound transducer 71). This volume within the vessel lumen adjacent the stenotic lesion 36 may or may not introduce too much error into the pressure drop measurement, depending on the size of the leads, the size of the vessel, the size of the stenotic lesion 36, and other factors.

Figure 11A:
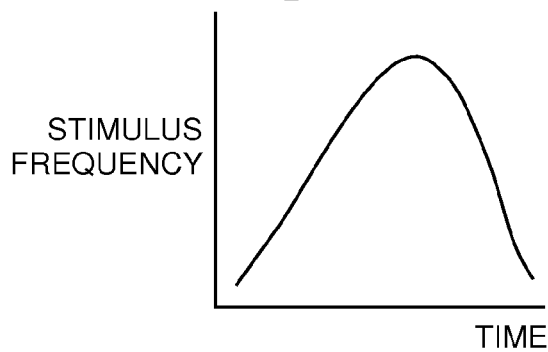
FIG. 11A is an illustrative waveform of the frequency of a stimulus signal with respect to time for multiple ultrasound transducers.
Figure 11B:
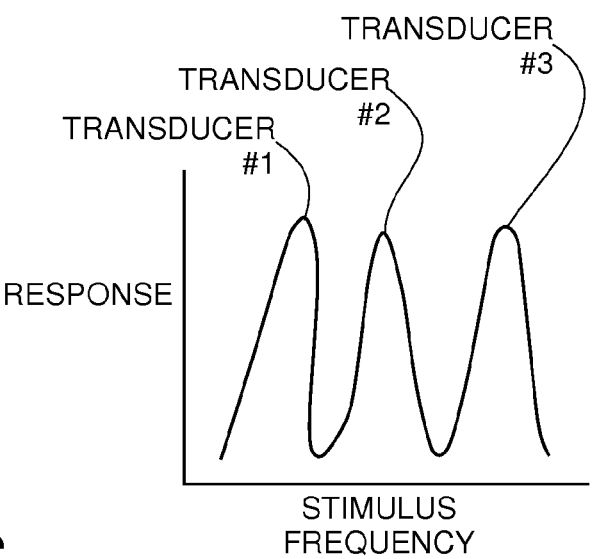
FIG. 11B is an illustrative waveform of how three different ultrasound transducers respond to a varying stimulus frequency.
Figure 11C:
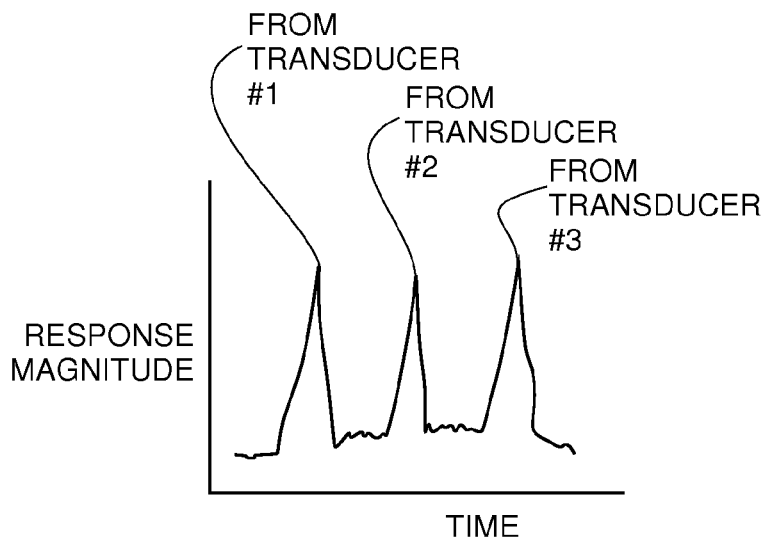
FIG. 11C is an illustrative waveform of the magnitude of a response signal coming from three different ultrasound transducers with respect to time.

FIGS. 11A-11C illustrate an embodiment having three individual ultrasound transducers each configured to emit ultrasound energy at different stimulus frequencies. As the stimulus signal is varied (FIG. 11A), the time at which the stimulus signal frequency triggers each of the three individual ultrasound transducers may be recorded. In analyzing the response signal (FIG. 11B), it may be assumed that the first peak corresponds to the first transducer to have been triggered, the second peak corresponds to the second transducer to have been triggered, and the third peak corresponds to the third transducer to have been triggered. The peaks may signify that the ultrasound energy has reflected off of the vessel wall rather than the fluid flowing through the vessel. The radial distance between each ultrasound transducer and the vessel wall can be based on the time that elapses between when it is triggered and when its first peak response signal is received, along with the respective radial positions of the ultrasound transducers. That radial distance can be based on properties of the fluid flowing through the vessel (e.g., how fast ultrasound energy travels through the fluid). Many calculations of distance account for ultrasonic dispersion effects.

Figure 12A:
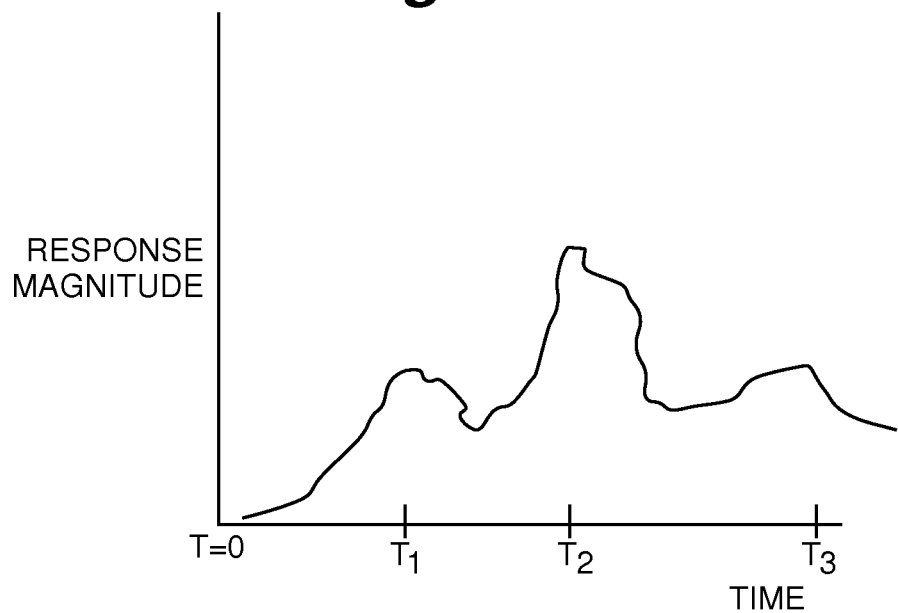
FIG. 12A is an illustrative waveform of the magnitude of a response signal coming from three different ultrasound transducers with respect to time.
Figure 12B:
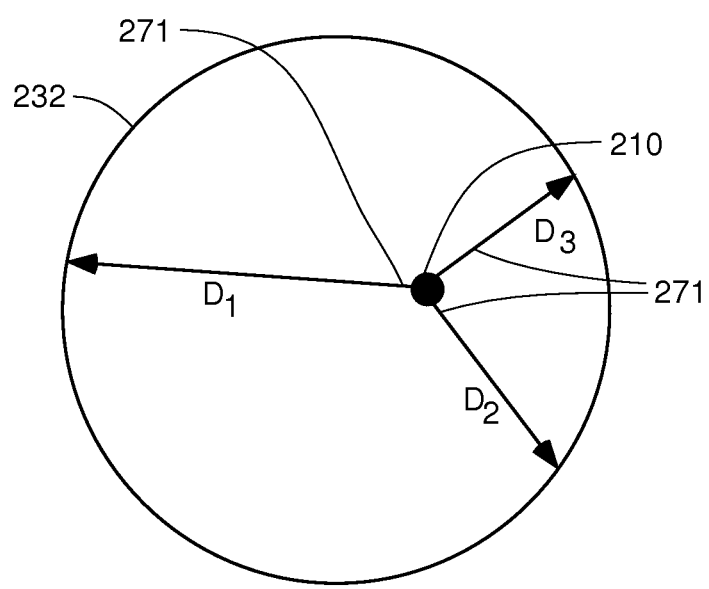
FIG. 12B is an end view of a patient's vessel with a vessel sensing system in accordance with embodiments of the present invention.

FIGS. 12A-12B illustrate an embodiment having three individual ultrasound transducers each configured to emit ultrasound energy at roughly the same stimulus frequency. FIG. 12B shows a vessel sensing system 210 that carries three individual ultrasound transducers 271 and is positioned within a vessel 232. In some embodiments, the response signal(s) may be analyzed to estimate an average interior diameter of the vessel 232. For example, $$D_{avg} = \frac{2}{3}(D_1+D_2+D_3)+D_{vss}$$

and $\frac{2}{3}(D_1+D_2+D_3)$ is proportional to $\frac{2}{3}(T_1+T_2+T_3)$ where $D_{avg}$ is the average interior diameter of the relevant axial location; $D_1$, $D_2$, and $D_3$ are the distances calculated based on the response signals from each ultrasound transducer 271; $D_{vss}$ is the diameter of the vessel sensing system that carries the three individual ultrasound transducers 271; and $T_1$, $T_2$, and $T_3$ are times to the peaks in the return signal. In some instances, a vessel lumen can be modeled as having a circular cross-sectional profile, but it should be understood that vessel lumens can have a variety of cross-sectional profiles.

Figure 13:
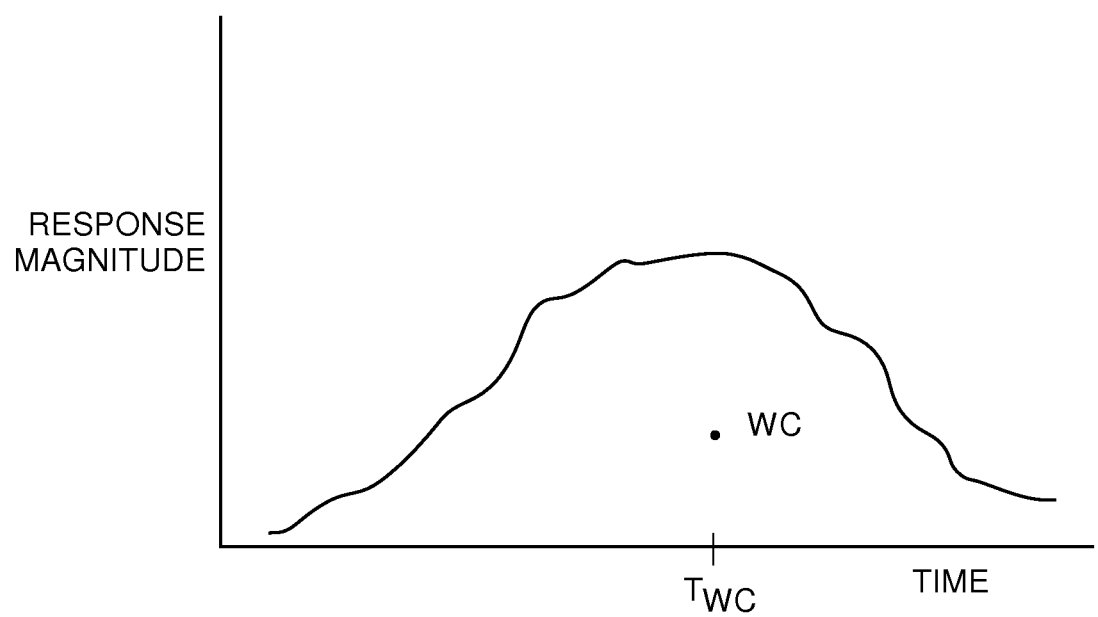
FIG. 13 is an illustrative waveform of the magnitude of a response signal coming from an ultrasound transducer ring with respect to time.

FIG. 13 illustrates an embodiment having an ultrasound transducer ring that emits ultrasound energy radially in a generally uniform manner. In some embodiments, a weighted center WC under the response signal curve may be determined according to known methods. The time $T_{WC}$ that corresponds to the weighted center WC can be used to estimate the average distance from the ultrasound transducer ring to the lesion at the associated axial location. When such a waveform is relatively narrow, it may be inferred that the ultrasound transducer ring is roughly centered within the patient's vessel. When such a waveform is relatively broad, it may be inferred that the ultrasound transducer ring is not centered within the patient's vessel.

In the foregoing detailed description, the invention has been described with reference to specific embodiments. However, it may be appreciated that various modifications and changes can be made without departing from the scope of the invention. Thus, some of the features of preferred embodiments described herein are not necessarily included in preferred embodiments of the invention which are intended for alternative uses.

The invention claimed is:

1. An intravascular transducer delivery device comprising:
    a distal sleeve having a guidewire lumen for slidably receiving a medical guidewire;
    a proximal portion coupled to the distal sleeve; and
    an ultrasound transducer coupled to the distal sleeve and/or the proximal portion, the ultrasound transducer comprising:
    an ultrasound ring transmitter; and
    an ultrasound ring receiver adjacent the ultrasound ring transmitter, wherein the ultrasound ring receiver includes first, second, and third receiver elements positioned about a circumference of the distal sleeve and/or the proximal portion.

2. The intravascular transducer delivery device of claim 1, wherein the first receiver element, the second receiver element, and the third receiver element are coupled to the distal sleeve.

3. The intravascular transducer delivery device of claim 1, wherein the first receiver element, the second receiver element, and the third receiver element are coupled to the distal sleeve.

4. The intravascular transducer delivery device of claim 1, further comprising a first pressure transducer coupled to the distal sleeve and/or the proximal portion, the first pressure transducer adapted to take a first intravascular fluid pressure measurement and generate a first pressure signal representative of the first intravascular fluid pressure measurement.

5. The intravascular transducer delivery device of claim 4, wherein the first pressure transducer is a fiber optic pressure transducer.

6. The intravascular transducer delivery device of claim 4, further comprising:
  (i) a second pressure transducer coupled to the distal sleeve and/or the proximal portion, the second pressure transducer adapted to take a second intravascular fluid pressure measurement and generate a second pressure signal representative of the second intravascular fluid pressure measurement,
  wherein the second pressure transducer is spaced longitudinally from the first pressure transducer by a distance that corresponds to a stenotic lesion.

7. The intravascular transducer delivery device of claim 4, wherein the first receiver element, the second receiver element, and the third receiver element are positioned distal to the first pressure transducer.

8. The intravascular transducer delivery device of claim 1, further comprising one or more transducer conductors in communication with the ultrasound transducer, wherein the one or more transducer conductors are configured to provide a stimulus signal to the ultrasound ring transmitter, and wherein the one or more transducer conductors are adapted to communicate a first ultrasound signal received at the first receiver element, a second ultrasound signal received at the second receiver element, and a third ultrasound signal received at the third receiver element, outside of a patient through the proximal portion.

9. The intravascular transducer delivery device of claim 1, wherein the one or more transducer conductors comprise a single ultrasound transducer conductor configured to provide the stimulus signal at respective distinct frequencies to the first ultrasound transducer, the second ultrasound transducer, and the third ultrasound transducer and adapted to communicate the first ultrasound signal, the second ultrasound signal, and the third ultrasound signal outside of the patient through the proximal portion.

10. The intravascular transducer delivery device of claim 8, wherein the first ultrasound signal, the second ultrasound signal, and the third ultrasound signal each comprise distinct frequencies from one another based on respective distinct frequencies of the provided stimulus signal; wherein the first ultrasound signal is representative of a first intravascular distance value, the second ultrasound signal is representative of a second intravascular distance value, and the third ultrasound signal is representative of a third intravascular distance value.

11. The intravascular transducer delivery device of claim 10, wherein the first intravascular distance value, the second intravascular distance value, and the third intravascular distance value each comprise a radial distance from the first receiver element, the second receiver element, and the third receiver element to a vessel or lesion wall, respectively.

* * * * *